(12) United States Patent
Nösel

(10) Patent No.: US 7,169,147 B2
(45) Date of Patent: Jan. 30, 2007

(54) URETER RESECTOSCOPE

(75) Inventor: Bernd Nösel, Lütjensee (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 142 days.

(21) Appl. No.: 10/840,823

(22) Filed: May 7, 2004

(65) Prior Publication Data
US 2004/0242959 A1  Dec. 2, 2004

(30) Foreign Application Priority Data
May 30, 2003 (DE) .................. 103 24 704

(51) Int. Cl.
*A61B 18/14* (2006.01)
*A61B 10/04* (2006.01)
*A61B 1/307* (2006.01)

(52) U.S. Cl. .................. 606/46; 600/104; 600/105; 600/106

(58) Field of Classification Search .......... 606/46; 600/104–106
See application file for complete search history.

(56) References Cited

U.S. PATENT DOCUMENTS

| | | | | |
|---|---|---|---|---|
| 4,134,406 A * | 1/1979 | Iglesias | ...................... | 606/46 |
| 4,474,174 A * | 10/1984 | Petruzzi | ...................... | 600/104 |
| 4,618,885 A * | 10/1986 | Nagasaki et al. | ............ | 348/74 |
| 4,726,370 A * | 2/1988 | Karasawa et al. | ............ | 606/46 |
| 4,776,336 A * | 10/1988 | Karasawa | .................... | 606/46 |
| 5,007,907 A * | 4/1991 | Nishigaki et al. | ............ | 606/46 |
| 5,919,191 A * | 7/1999 | Lennox et al. | ................. | 606/48 |
| 5,935,125 A * | 8/1999 | Zupkas | ........................ | 606/46 |
| 5,938,661 A * | 8/1999 | Hahnen | ....................... | 606/46 |
| 6,699,185 B2 * | 3/2004 | Gminder et al. | ............ | 600/157 |
| 2001/0053908 A1 * | 12/2001 | Brommersma et al. | ....... | 606/45 |
| 2003/0144662 A1 | 7/2003 | Wosnitza et al. | ............. | 606/46 |
| 2004/0044343 A1 * | 3/2004 | Brommersma et al. | ....... | 606/46 |

FOREIGN PATENT DOCUMENTS

| JP | 62-87619 | 6/1987 |
|---|---|---|
| JP | 1-75416 | 5/1989 |

* cited by examiner

*Primary Examiner*—Michael Peffley
*Assistant Examiner*—Alex Toy
(74) *Attorney, Agent, or Firm*—Rankin, Hill, Porter & Clark LLP

(57) ABSTRACT

A ureter resectoscope with an elongate flexible stem tube (4) of substantial length and small external diameter, of which the distal end piece (5) is made from insulating material and which accommodates an optical unit (6) as well as a rod-shaped instrument carrier (11). The instrument carrier is disposed so as to be longitudinally displaceable parallel to the optical unit and bears on its distal end an electrode (12, 12') that can be supplied with high-frequency current and, on its proximal end after passing through a bore in a main body (1) disposed on the proximal end of the stem tube, is fixed and electrically contacted on a slider (13) mounted so as to longitudinally displaceable. The instrument carrier is guided in the vicinity of its distal end on the optical unit (6) by a sliding tube (20) A stop (19) is disposed on the optical unit (6) proximally from the sliding tube (20) in a position which, with the instrument carrier (11) retracted until the sliding tube (20) is in abutment against the stop (19), results in a sufficient electrical safety distance between the electrode (12) and the distal top of the optical unit (6).

12 Claims, 2 Drawing Sheets

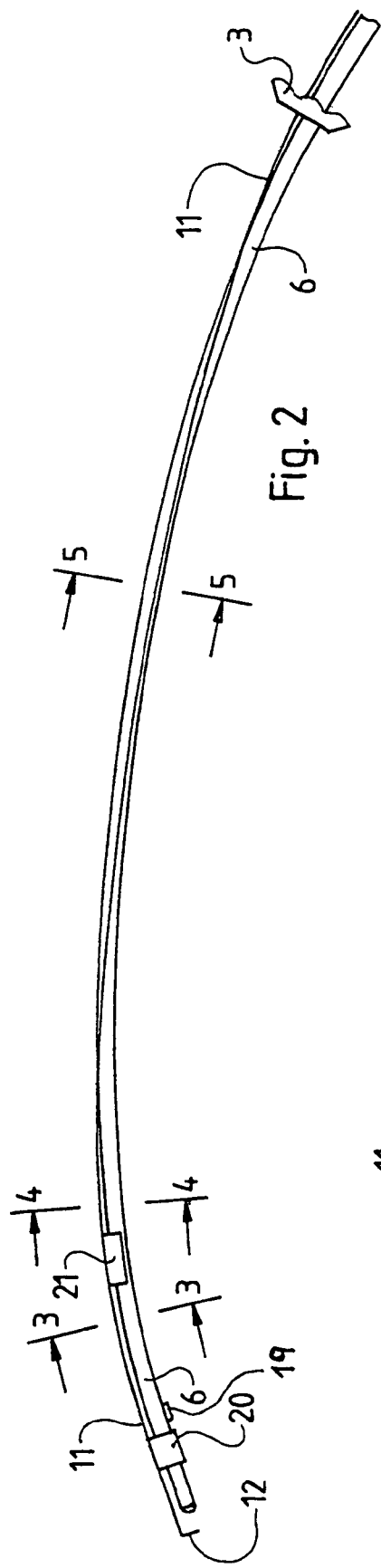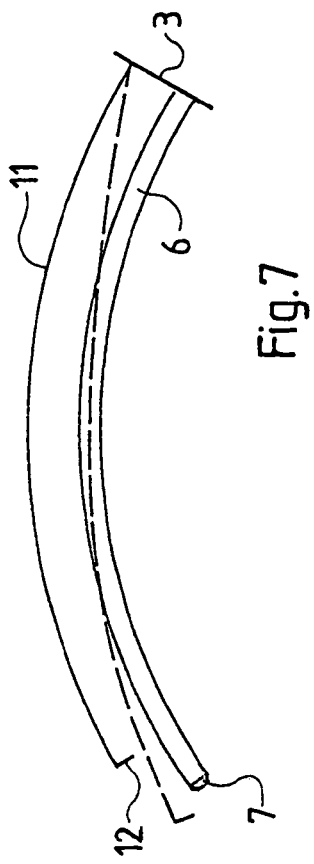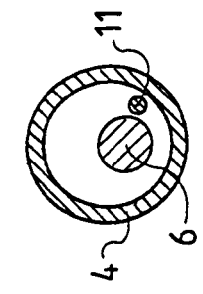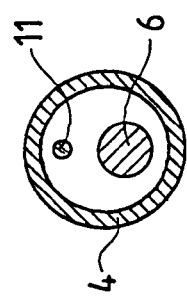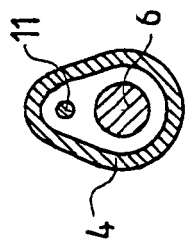

URETER RESECTOSCOPE

BACKGROUND OF THE INVENTION

1. Field of the Invention

The invention relates to a ureter resectoscope with an elongate flexible stem tube of substantial length and small external diameter that bears on its distal end an electrode that can be supplied with high-frequency current and on its proximal end is fixed and electrically contacted on a slider mounted so as to be longitudinally displaceable.

2. Description of Related Art

The basic design of generic ureter resectoscopes corresponds to that of the normal urological resectoscope, which is used principally for prostate resection. For this purpose the normal resectoscope only needs to be introduced a short distance through the urethra and thus can have a relatively large diameter with a relatively short stem length.

However, the ureter resectoscope is used in the ureter, that is to say the narrow body channel between the bladder and the kidney. Therefore, it must be substantially longer and thinner than the normal resectoscope. The stem typically has a length of 40 cm and a diameter of at most 3–4 mm. Moreover, the stem must be flexible, since for anatomical reasons it must be greatly bent during introduction.

However, the mode of operation of the ureter resectoscope should correspond as closely as possible to that of the normal resectoscope. Thus, an electrode supplied with high-frequency current with an instrument carrier is moved along in the visual range of the optical unit in order to be able to cut tissue. In this case the usual cutting loop, which cuts as it is retracted against the distal edge of the insulating distal end piece of the stem tube, is used.

For reasons of space in the narrow stem tube, in the ureter resectoscope the rod-shaped instrument carrier is mounted in the same angular position parallel to the optical unit over the entire length of the stem tube. Thus, when the stem tube is bent, the optical unit and the instrument carrier extending parallel thereto are bent at different radii, so the direction of bending is significant. If the instrument carrier lies above the optical unit and is bent laterally, then the bending radii are the same. If the distal end of the stem tube is bent upwards, then the bending radius of the instrument carrier is smaller, so that with the enforced parallel guiding in the stem tube and with the fixed proximal end of the instrument carrier the distal end thereof moves forwards. If the stem tube is bent downwards at its distal end, then the bending radius of the instrument carrier is greater than that of the optical unit, resulting in a shortening of the instrument carrier, so that with the fixed proximal end of the instrument carrier the distal end thereof is drawn with the electrode in the proximal direction.

With the bending direction last described above there is an electrical safety problem. If the electrode is greatly bent, the electrode can be retracted to such an extent that it touches the optical unit or comes too close to the optical unit. Since the optical unit does not usually have any special insulation provisions, when the electrode is supplied with high frequency current this can lead to a current flashover and, thus, to a current flow through the optical unit to the entire device. The consequences are burns to the patient and to the operator. This safety problem always occurs when the instrument carrier with the slider on which it is fixed is drawn in the proximal direction until the slider reaches a stop. Depending upon the design of the slider actuation means, this is the rest position of the slider or the slider may be drawn by the transporter out of the rest position and into the proximal stop position.

Therefore, there exists a need in the art for improved electrical safety for ureter resectoscopes.

SUMMARY OF THE INVENTION

The present invention is directed toward improving the electrical safety of the generic ureter resectoscope in a simple manner.

According to the invention there is provided on the optical unit a stop against which the slide tube of the instrument carrier comes into abutment when the instrument carrier is retracted. In this case, the stop is positioned such that when the slide tube is in abutment against the stop a safe distance between the electrode and the optical unit is ensured. Once the stop is in abutment with the slide tube, the electrode cannot be retracted further, so that electrical safety is ensured by simple means, even when the stem of the ureter resectoscope is greatly bent in an unfavourable direction, so that the electrode is retracted relative to the optical unit.

In this unfavourable bending direction, when the slider is retracted the slide tube comes into abutment with the stop. The slider can then no longer be moved into its proximal end position, and thus the working stroke of the electrode is shortened. If the slider should nevertheless remain held at its proximal abutment, then the stem region of the ureter resectoscope cannot be bent to the desired extent.

In further accordance with the present invention, since the instrument carrier can be displaced laterally around the optical unit in the stem region proximally from its distal region, it can take a shorter path in which the distance between the distal end of the optical unit and the slider is shorter. As a result, the electrode is retracted less far by the bending of the stem region. The stem region of the ureter resectoscope can be very greatly bent to the desired extent and the full stroke is again available for the slider. Thus, the ureter resectoscope can be used in a very curved position without disruption.

In further accordance with the present invention, an additional guide tube can, like the guide tube also, be pushed over the optical unit from the distal end during assembly, so that the slot allows the stop on the optical unit to come through. The additional guide tube provides additional guiding in the distal region of the stem tube and also prevents twisting of the electrode if the instrument carrier moves laterally around the optical unit in the proximal region.

BRIEF DESCRIPTION OF THE DRAWINGS

The invention is illustrated schematically by way of example in the drawings, in which:

FIG. 2 shows the stem region of the ureter resectoscope of FIG. 1 without the stem tube and in a bent position, FIG. 3 is a cross-sectional view of the ureter resectoscope as seen along line 3—3 of FIG. 2, FIG. 4 is a cross-sectional view of the ureter resectoscope as seen along line 4—4 of FIG. 2

FIG. 5 is a cross-sectional view of the ureter resectoscope as seen along line 5—5 of FIG. 2

FIG. 6 shows the distal end region of the instrument carrier of FIG. 1 with an alternative electrode, and FIG. 7 shows a schematic representation of the bending relationships.

DETAILED DESCRIPTION OF THE PREFERRED EMBODIMENTS

Figure 1:
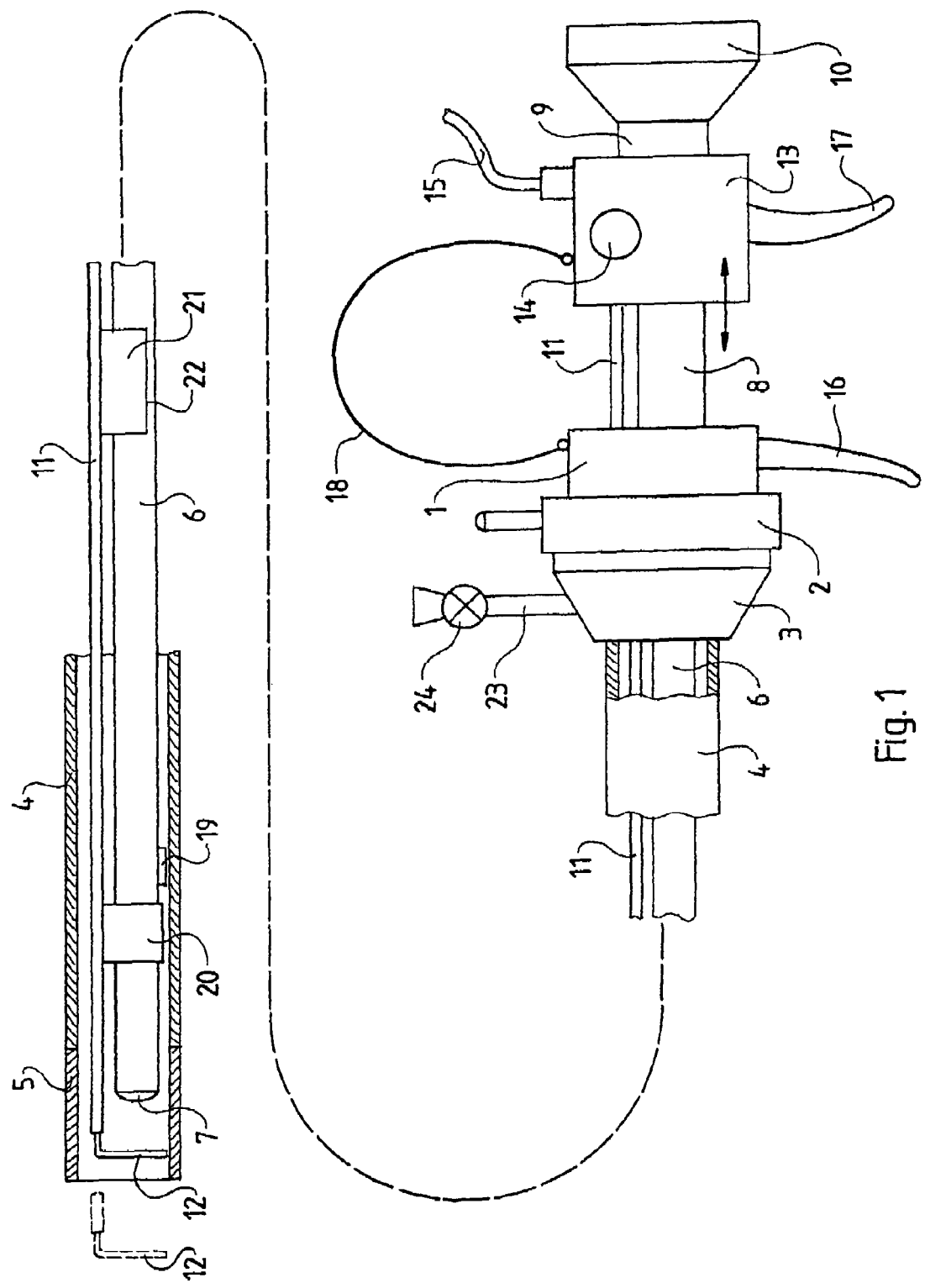
FIG. 1 shows a ureter resectoscope according to the invention in a partially section side view.

FIG. 1 shows the construction of a ureter resectoscope according to the invention. The coupling piece 3 of a stem tube 4 is coupled to a main body 1 with a coupling ring 2. The stem tube 4 has a length of for example 40 cm, which is usual for ureter resectoscopes, and an external diameter of a maximum of 4 mm. The distal end piece of the stem tube is constructed as an insulating body 5, for example of ceramic material.

An optical unit 6 of suitable very small diameter and with high flexibility extends in the interior of the stem tube 4 and ends with its objective 7 in the region of the insulating body 5. The optical unit 6 passes in the proximal direction through the stem tube 4, the main body 1, and an optical unit guide tube 8 attached to the main body with an end plate 9 disposed on the proximal end thereof, and ends in an eyepiece 10, at the location of which a video camera, for example, can also be provided.

A thin rod-shaped instrument carrier 11 passes parallel to the optical unit 6 through the stem tube 4. At its distal end the instrument carrier 11 bears an electrode 12 in the form of the usual cutting loop made from wire, as illustrated. The connecting lead for the electrode 12 runs through the instrument carrier 11, which is constructed so as to be externally insulating. After passing through a bore in the main body 1, the instrument carrier 11 extends as far as a slider 13. The proximal end of the instrument carrier 11 is fixed in the slider 13 with a fixing means 14 and the connecting lead in the interior of the instrument carrier 11 is contacted with a connecting cable 15 in the slider 13.

Finger grips 16, 17 are disposed on the main body 1 and on the slider 13, respectively. Furthermore, the main body 1 and the slider 13 are connected by way of a spring 18. In these design details the ureter resectoscope corresponds largely to the usual urological resectoscope.

By taking hold of the finger grips 16 and 17 the operator can move the slider 13 forwards, and the slider 13 is then moved back into abutment on the end plate 9 by the spring 18. In this case, as FIG. 1 shows, the electrode 12 is moved forwards as far as the position indicated by broken lines and is retracted again into the position shown by solid lines in FIG. 1. In this case the electrode 12, which is supplied with high frequency current, can cut off tissue lying in front of the insulating body 5.

In an alternative, conventional construction of the ureter resectoscope the slider 13 can be in abutment on the main body 1 in the rest position. In this case the finger grips 16, 17 are disposed on the slider 13 and on the end plate 9, and the spring 18 is disposed between the slider 13 and the end plate 9. In this case in the rest position the electrode 12 is in the position shown by broken lines in FIG. 1 and is moved by retraction of the slider 13 into the position shown by solid lines in FIG. 1 in abutment against the end plate 9.

In the position shown by solid lines, the electrode 12 lies as far as possible in the proximal direction with the slider 13 in abutment against the end plate 9. In this case the electrode 12 is a sufficient safety distance from the optical unit 6, so that there is no fear of current flashovers.

The situation is different if the stem of the illustrated ureter resectoscope is bent as shown in FIG. 2. In this case, with the instrument carrier 11 lying parallel above the optical unit 6, the distal end of the optical unit 6 is bent downwards. Consequently, the instrument carrier 11 lies on a longer path. Since its proximal end with the slider 13 is held in abutment against the end plate 9, the electrode 12 must retract.

In order to prevent this, as FIG. 1 shows, a stop 19 is fixed on the optical unit 6. Distally from the stop 19 the instrument carrier 11 is guided so as to be longitudinally displaceable with a sliding tube 20 on the optical unit 6. In the case of the shortening of the instrument carrier 11 relative to the optical unit 6, as just described and as illustrated in FIG. 2, that is to say when the distal end region of the instrument carrier 11 is retracted relative to the optical unit 6, the sliding tube 20 comes into abutment on the stop 19 and prevents further retraction. In this case the position of the stop 19 relative to the sliding tube 20 is chosen such that upon abutment a sufficient safety distance is maintained between the electrode 12 and the optical unit 6.

If after reaching the stop arrangement 19/20 the instrument carrier 11 were still to have to remain strictly parallel and in the same angular position relative to the optical unit 6, then the stem tube 4 could not be bent any further, or the slider 13 would be drawn in the distal direction and the full displacement path for the slider 13, that is to say the full working stroke for the electrode 12, would no longer be available.

In order, nevertheless, to facilitate a further free deformability of the stem tube 4 with an unaltered working stroke of the electrode 12, the interior of the stem tube in the central and proximal region is of a wide shape such that, as FIG. 2 shows in the region of the section 5, the instrument carrier can move laterally past the optical unit 6 (FIG. 5). Due to this deflection movement the length of travel of the instrument carrier 11 shortens, so that the stem tube 4 can be bent further, even if the instrument carrier 11 is held at the distal end by the stop 19 and at the proximal end by the abutment of the slider 13 against the end plate 9.

FIG. 7 shows the bending relationships in a highly schematic fashion. The optical unit 6 and the instrument carrier 11 with its electrode 12 are shown here in highly schematic fashion, and for the purposes of explanation are shown jointly fixed with their proximal ends on the coupling piece 3. Both are shown with the same length. In the straight position of the optical unit 6 and the instrument carrier 11, the electrode 12 would therefore lie in front of the objective 7. In FIG. 7 the optical unit 6 and the instrument carrier 11 are shown greatly bent downwards. It can be seen that in this case the electrode 12 is retracted relative to the objective 7 if the parallel positions of the optical unit 6 and the instrument carrier 11 are maintained.

In FIG. 7 broken lines show the position of the instrument carrier 11 when it can relinquish its parallel position relative to the optical unit 6 and can be displaced laterally around the latter. Then it lies on a shorter path and is again with the electrode 12 at the level of the optical unit 7.

In the usual construction of ureter resectoscopes, the stem tube 4 is of oval construction in its distal end region and closely adapted to the cross-sections of the optical unit 6 and of the instrument carrier 11. However, in the proximal direction the internal cross-section of the stem tube widens and assumes a round shape, as the sections in FIGS. 4 and 5 show. As a result, as FIG. 5 shows, space is created in this region for the lateral displacement of the instrument carrier 11.

For additionally securing the electrode 12 against twisting during lateral displacement of the instrument carrier 11 in accordance with FIG. 5, in addition to the sliding tube 20 an additional sliding tube 21 set back proximally is provided with which the instrument carrier 11 is mounted so as to be longitudinally displaceable on the optical unit 6 (FIG. 2). The additional sliding tube 21 has a longitudinal slot 22 in the angular position in which the stop 19 is disposed on the optical unit 6. This makes it possible for both sliding tubes 20 and 21 to be pulled off from the optical unit 6 in the distal direction for dismantling.

Instead of the electrode 12 shown in FIG. 1 in the form of a conventional cutting loop, another electrode 12' in knife form can also be provided, as FIG. 6 shows. Such a knife can also optionally be used cold, that is to say without high-frequency current supply.

As FIG. 1 shows, a lateral tube 23 with a valve 24 can be provided on the coupling piece 3, this tube being connected inwardly to the interior of the stem tube 4 and used for example for rinsing purposes.

The invention claimed is:

1. A ureter resectoscope with an elongate flexible stem tube (4) of substantial length and small external diameter, of which a distal end piece (5) is made from insulating material and which accommodates an optical unit (6) as well as a rod-shaped instrument carrier (11) that is disposed so as to be longitudinally displaceable parallel to the optical unit, said instrument carrier bearing, on its distal end, an electrode (12, 12') that can be supplied with high-frequency current and, on its proximal end after passing through a bore in a main body (1) disposed on a proximal end of the stem tube, is fixed and electrically contacted on a slider (13) mounted so as to be longitudinally displaceable, wherein the instrument carrier is guided in the vicinity of its distal end on the optical unit (6) by a sliding tube (20), and wherein on the optical unit (6) proximally from the sliding tube (20) a stop (19) is disposed in a position, which, with the instrument carrier (11) retracted until the sliding tube (20) is in abutment against the stop (19), results in a sufficient electrical safety distance between the electrode (12) and the distal top of the optical unit (6).

2. The ureter resectoscope as claimed in claim 1, wherein an internal cross-section of the stem tube (4) proximally from its distal region is sufficiently dimensioned in order to allow a lateral displacement of the instrument carrier (11) around the optical unit (6).

3. The ureter resectoscope as claimed in claim 1, wherein the instrument carrier (11) is guided on the optical unit (6) with a proximal spacing from the sliding tube (20) by an additional sliding tube (21), which is slotted in the angular region of the stop (19).

4. The ureter resectoscope as claimed in claim 1, wherein the elongate flexible stem tube has a length of about 40 cm and a diameter not exceeding 4 mm.

5. A ureter resectoscope with an elongate flexible stem tube (4) of substantial length and small external diameter, of which a distal end piece (5) is made from insulating material and which accommodates an optical unit (6) as well as a rod-shaped instrument carrier (11) that is disposed so as to be longitudinally displaceable parallel to the optical unit, said instrument carrier bearing, on its distal end, an electrode (12, 12') that can be supplied with high-frequency current and, on its proximal end after passing through a bore in a main body (1) disposed on a proximal end of the stem tube, is fixed and electrically contacted on a slider (13) mounted so as to be longitudinally displaceable, wherein the instrument carrier is guided in the vicinity of its distal end on the optical unit (6) by a sliding tube (20), and wherein immovably affixed to the optical unit (6), proximally from the sliding tube (20), a stop (19) is disposed in a position, which, with the instrument carrier (11) retracted until the sliding tube (20) is in abutment against the stop (19), results in a sufficient electrical safety distance between the electrode (12) and the distal top of the optical unit (6).

6. The ureter resectoscope as claimed in claim 5, wherein an internal cross-section of the stem tube (4) proximally from its distal region is sufficiently dimensioned in order to allow a lateral displacement of the instrument carrier (11) around the optical unit (6).

7. The ureter resectoscope as claimed in claim 5, wherein the instrument carrier (11) is guided on the optical unit (6) with a proximal spacing from the sliding tube (20) by an additional sliding tube (21), which is slotted in the angular region of the stop (19).

8. The ureter resectoscope of claim 5 wherein the elongate flexible stem tube has a length of about 40 cm and a diameter not exceeding 4 mm.

9. A ureter resectoscope with an elongate flexible stem tube (4) of substantial length and small external diameter, of which a distal end piece (5) is made from insulating material and which accommodates an optical unit (6) as well as a rod-shaped instrument carrier (11) that is disposed so as to be longitudinally displaceable parallel to the optical unit, said instrument carrier bearing, on its distal end, an electrode (12, 12') that can be supplied with high-frequency current and, on its proximal end after passing through a bore in a main body (1) disposed on a proximal end of the stem tube, is fixed and electrically contacted on a slider (13) mounted so as to be longitudinally displaceable, wherein the instrument carrier is guided in the vicinity of its distal end on the optical unit (6) by a sliding tube (20), and wherein the optical unit (6) is slidably engaged within and guided at its proximal end by a guide tube (8) that distally terminates near the proximal end of the stem tube (4), and wherein on the optical unit (6) proximally from the sliding tube (20) a stop (19) is disposed in a position, which, with the instrument carrier (11) retracted until the sliding tube (20) is in abutment against the stop (19), results in a sufficient electrical safety distance between the electrode (12) and the distal top of the optical unit (6).

10. The ureter resectoscope as claimed in claim 9, wherein an internal cross-section of the stem tube (4) proximally from its distal region is sufficiently dimensioned in order to allow a lateral displacement of the instrument carrier (11) around the optical unit (6).

11. The ureter resectoscope as claimed in claim 9, wherein the instrument carrier (11) is guided on the optical unit (6) with a proximal spacing from the sliding tube (20) by an additional sliding tube (21), which is slotted in the angular region of the stop (19).

12. The ureter resectoscope of claim 9 wherein the elongate flexible stem tube has a length of about 40 cm and a diameter not exceeding 4 mm.

* * * * *